(12) United States Patent
Harashima et al.

(10) Patent No.: US 10,182,987 B2
(45) Date of Patent: Jan. 22, 2019

(54) LIPID MEMBRANE STRUCTURE FOR INTRACELLULAR DELIVERY OF SIRNA

(71) Applicant: NATIONAL UNIVERSITY CORPORATION HOKKAIDO UNIVERSITY, Hokkaido (JP)

(72) Inventors: Hideyoshi Harashima, Hokkaido (JP); Yusuke Sato, Hokkaido (JP); Shota Warashina, Hokkaido (JP); Hiroto Hatakeyama, Hokkaido (JP); Mamoru Hyodo, Hokkaido (JP); Takashi Nakamura, Hokkaido (JP)

(73) Assignee: NATIONAL UNIVERSITY CORPORATION HOKKAIDO UNIVERSITY, Sapporo-shi (JP)

(*) Notice: Subject to any disclaimer, the term of this patent is extended or adjusted under 35 U.S.C. 154(b) by 95 days.

(21) Appl. No.: 15/311,644

(22) PCT Filed: May 18, 2015

(86) PCT No.: PCT/JP2015/064196
§ 371 (c)(1),
(2) Date: Feb. 21, 2017

(87) PCT Pub. No.: WO2015/178343
PCT Pub. Date: Nov. 26, 2015

(65) Prior Publication Data
US 2017/0273905 A1    Sep. 28, 2017

(30) Foreign Application Priority Data
May 20, 2014  (JP) .............................. 2014-104131

(51) Int. Cl.
| | | |
|---|---|---|
| A61K 48/00 | (2006.01) | |
| A61K 9/127 | (2006.01) | |
| C12N 15/113 | (2010.01) | |
| C12N 15/88 | (2006.01) | |
| A61K 9/12 | (2006.01) | |
| A61K 47/18 | (2017.01) | |
| A61K 31/7105 | (2006.01) | |
| A61K 35/12 | (2015.01) | |
| C07C 215/08 | (2006.01) | |
| A61K 39/00 | (2006.01) | |
| A61K 39/39 | (2006.01) | |
| A61K 47/42 | (2017.01) | |
| A61K 47/48 | (2006.01) | |
| C12N 15/00 | (2006.01) | |
| C12N 15/09 | (2006.01) | |
| C12N 15/63 | (2006.01) | |

(52) U.S. Cl.
CPC ............... *A61K 9/12* (2013.01); *A61K 9/127* (2013.01); *A61K 9/1271* (2013.01); *A61K 31/7105* (2013.01); *A61K 35/12* (2013.01); *A61K 39/0012* (2013.01); *A61K 39/39* (2013.01); *A61K 47/18* (2013.01); *A61K 47/42* (2013.01); *A61K 47/48* (2013.01); *A61K 47/48238* (2013.01); *A61K 47/48815* (2013.01); *A61K 47/48838* (2013.01); *A61K 48/00* (2013.01); *A61K 48/005* (2013.01); *A61K 48/0041* (2013.01); *C07C 215/08* (2013.01); *C12N 15/113* (2013.01); *C12N 15/88* (2013.01); A61K 2039/55555 (2013.01); A61K 2039/6018 (2013.01); A61K 2039/6025 (2013.01); *C12N 15/00* (2013.01); *C12N 15/09* (2013.01); *C12N 15/63* (2013.01)

(58) Field of Classification Search
CPC .. A61K 6/00; A61K 9/127; A61K 2039/6018; C12N 15/88; C12N 15/113
USPC ....... 435/6.1, 91.1, 91.31, 455, 458; 514/44; 536/23.1, 24.5
See application file for complete search history.

(56) References Cited

U.S. PATENT DOCUMENTS

2017/0152528 A1* 6/2017 Zhang .................. C12N 15/907

FOREIGN PATENT DOCUMENTS

| | | |
|---|---|---|
| JP | 2006-28030 A | 2/2006 |
| JP | 2013-533223 A | 8/2013 |
| JP | 2013-545723 A | 12/2013 |
| JP | 2013-545727 A | 12/2013 |
| JP | 2013245190 A | 12/2013 |
| JP | 2014-500233 A | 1/2014 |
| WO | 2005/032593 A1 | 4/2005 |
| WO | 2006007712 A | 1/2006 |
| WO | 2006/101201 A1 | 9/2006 |
| WO | 2007/102481 A1 | 9/2007 |

(Continued)

OTHER PUBLICATIONS

Hidetaka Akita et al., "Development of multifunctional envelope-type nano-device (MEND) based on the regulation of intracellular trafficking", Drug Delivery System, 22-2, 2007, pp. 115-122.
Nanda K. Subbarao et al., "pH-Dependent Bilayer Destabilization by an Amphipathic Peptide", Biochemistry, 26, 1987, pp. 2964-2972.
Tomoyuki Kakudo et al., "Transferrin-Modified Liposomes Equipped with a pH-Sensitive Fusogenic Peptide: An Artificial Viral-like Delivery System", Biochemistry, 43, 2004, pp. 5618-5623.

(Continued)

*Primary Examiner* — Jane J Zara
(74) *Attorney, Agent, or Firm* — Birch, Stewart, Kolasch & Birch, LLP

(57) ABSTRACT

A lipid membrane structure encapsulating an siRNA inside thereof and containing a lipid compound of the formula (I) as a lipid component ($R^1$ and $R^2$ represent $CH_3-(CH_2)_n-CH=CH-CH_2-CH=CH-(CH_2)_m-$, n represents an integer of 3 to 5, m represents an integer of 6 to 10, p represents an integer of 2 to 7, and $R^3$ and $R^4$ represent a $C_{1-4}$ alkyl group or a $C_{2-4}$ alkenyl group.

19 Claims, 8 Drawing Sheets

(56) References Cited

FOREIGN PATENT DOCUMENTS

| WO | 2011/132713 A1 | 10/2011 | |
|---|---|---|---|
| WO | WO 2012/068176 | * | 5/2012 |
| WO | 2013/158579 A1 | 10/2013 | |

OTHER PUBLICATIONS

Tara B. Wyman et al., "Design, Synthesis, and Characterization of a Cationic Peptide That Binds to Nucleic Acids and Permeabilizes Bilayers", Biochemistry, 36, 1997, pp. 3008-3017.
Kentaro Kogure et al., "Development of a non-viral multifunctional envelope-type nano device by a novel lipid film hydration method", Journal of Controlled Release, 98, 2004, pp. 317-323.
Lei Shen et al., "Silencing of SOCS1 enhances antigen presentation by dendritic cells and antigen-specific anti-tumor immunity", Nature Biotechnology, 22, 2004, pp. 1546-1553.
Xiao-Tong Song et al., "A20 is an antigen presentation attenuator, and its inhibition overcomes regulatory T cell-mediated suppression", Nature Medicine, 14, 2008, pp. 258-265.
Hidetaka Akita et al., "Nanoparticles for ex vivo siRNA delivery to dendritic cells for cancer vaccines: Programmed endosomal escape and dissociation", "J. Control. Release, 143", 2010, pp. 311-317.
Shota Warashina et al., "A20 Silencing by Lipid Envelope-Type Nanoparticles Enhances the Efficiency of Lipopolysaccharide-Activated Dendritic Cells", Biol. Pharm. Bull., 34, 2011, pp. 1348-1357.
International Search Report and Written Opinion issued with respect to Application No. PCT/JP2015/064196, dated Aug. 11, 2015.
International Preliminary Report on Patentability issued with respect to Application No. PCT/JP20151064196, dated Nov. 22, 2016.
Extended European Search Report in respect to European Application No. 15796352.1, dated Dec. 15, 2017.

* cited by examiner bar : 20 μm

LIPID MEMBRANE STRUCTURE FOR INTRACELLULAR DELIVERY OF SIRNA

TECHNICAL FIELD

The present invention relates to a lipid membrane structure for intracellular delivery of siRNA. More specifically, the present invention relates to a lipid membrane structure such as liposome that is capable of achieving easy delivery of siRNA intracellularly into a nucleus of an immunocyte, especially into a dendritic cell.

BACKGROUND ART

As a means for transporting a medicament specifically to a pathological lesion, methods of encapsulating a medicament in liposomes have been proposed. In particular, in the field of therapeutic treatments of malignant tumors, many reports have been made as for effectiveness of liposomes encapsulating an antitumor agent. Further, a multifunctional envelope-type nano device (MEND: henceforth sometimes abbreviated as "MEND" in the specification, see, for example, Drug Delivery System, 22-2, pp. 115-122, 2007 and the like) has been proposed. This structure can be used as a drug delivery system for delivering a gene or the like selectively into particular cells, and is known to be useful for, for example, gene therapy of tumors and the like.

Variety of methods have been proposed for modifying the surface of a lipid membrane structure with a functional molecule, as means for delivering an objective substance such as medicaments, nucleic acids, peptides, polypeptides, and saccharides to specific parts such as target organs and tumor tissues using a lipid membrane structure. When a lipid membrane structure encapsulating a medicament such as antitumor agent reaches a target cell, the structure is taken up into the cell by endocytosis and encapsulated in the endosome. Then, the structure releases the encapsulated medicament into the cytoplasm due to hydrolytic action of an enzyme in the lysosome or the like. In order to enhance the release of medicament from a liposome taken up into the endosome, a liposome has been proposed of which surface is modified with a peptide, GALA (Biochemistry, 26, pp. 2964-2972, 1987 for the peptide; Biochemistry, 43, pp. 5618-5623, 2004 for the liposome) and MEND (Japanese Patent Unexamined Publication (KOKAI) No. 2006-28030).

Further, as means for localization of a lipid membrane structure encapsulating an objective substance such as nucleic acid into the nucleus of a target cell, there have been proposed, for example, a liposome of which outer surface is modified with octaarginine (International Patent Publication WO2005/32593; Journal of Controlled Release, 98, pp. 317-323, 2004), a bilamellar liposome having a lipid membrane modified with a nucleus permeable peptide (International Patent Publication WO2006/101201), and a liposome of which surface is modified with a monosaccharide such as galactose and mannose (International Patent Publication WO2007/102481). It has been reported that a multilamellar lipid membrane structure (T-MEND) modified with a monosaccharide has fusability with a lipid membrane and a nuclear membrane, and is capable of improving gene expression efficiency as an experimental result in vitro. It has further been reported that a lipid membrane structure modified with the KALA peptide (Biochemistry, 36, pp. 3008-3017, 1997) can efficiently deliver such a substance as a nucleic acid into a nucleus of a cell (WO2011/132713).

Dendritic cells are antigen-presenting cells responsible for the central part of immunological response, therefore they constitute one type of important target cells of cancer immunotherapies, and they are also used for immunocyte therapy (dendritic cell therapy), in which dendritic cells are extracted from a cancer patient, subjected to antigen introduction or activation outside the body, and then administered again to the patient. Since an immunosuppressive factor has been discovered in dendritic cells in recent years, they attract attention also as a target of siRNA medicaments, and it is expected that combination of them with the dendritic cell therapy shall realize more potent cancer immunity induction.

Concerning introduction of siRNA into nuclei of dendritic cells, there are former reports that an immunosuppressive factor was knocked down by using a lentivirus vector that expresses shRNA (Nat. Biotechnol., 2004; Nat. Med., 2008). However, there are almost no reports concerning introduction of siRNA into dendritic cells using an artificial delivery system. Although use of a virus vector can achieve efficient knockdown of a target gene, it has a problem from a viewpoint of safety.

As an artificial delivery system for introduction of siRNA, R8/GALA-D-MEND (D-MEND) has been reported (J. Control. Release, 143, pp. 311-317, 2010). D-MEND is a nano-carrier consisting of MEND of which envelope membrane number is controlled by modification with an octarginine (R8) peptide as a cellular affinity device and a GALA peptide as an endosomal escaping device. D-MEND gives about 70% of knockdown even at such a low siRNA concentration as 12 nM in HeLa cells, which are generally used cancer cells, and the activity thereof is twice or more higher than that of Lipofectamine 2000 (LFN2000), which is widely used as a general introduction reagent.

However, in the case of transfection with D-MEND into dendritic cells induced from mouse bone marrow cells, use of a high siRNA concentration (80 to 120 nM) is required in order to attain a knockdown efficiency of 70 to 80%, and it also suffers from a problem that the knockdown efficiency is limited to about 40% depending on the target factor of siRNA (Biol. Pharm. Bull., 34, pp. 1348-1351, 2011). As described above, use of a conventional artificial delivery system tends to markedly reduce the knockdown efficiency in dendritic cells, as compared with that obtainable in general cancer cells, and this fact hampers development of siRNA medicaments in the field of immunotherapy.

PRIOR ART REFERENCES

Patent Documents

Patent document 1: International Patent Publication WO2005/32593
Patent document 2: International Patent Publication WO2006/101201
Patent document 3: International Patent Publication WO2007/102481
Patent document 4: Japanese Patent Unexamined Publication (KOKAI) No. 2006-28030
Patent document 5: International Patent Publication WO2011/132713

Non-Patent Documents

Non-patent document 1: Drug Delivery System, 22-2, pp. 115-122, 2007
Non-patent document 2: Biochemistry, 26, pp. 2964-2972, 1987

Non-patent document 3: Biochemistry, 43, pp. 5618-5623, 2004
Non-patent document 4: Journal of Controlled Release, 98, pp. 317-323, 2004
Non-patent document 5: Biochemistry, 36, pp. 3008-3017, 1997
Non-patent document 6: Nat. Biotechnol., 22, pp. 1546-1553, 2004
Non-patent document 7: Nat. Med., 14, pp. 258-265, 2008
Non-patent document 8: J. Control. Release, 143, pp. 311-317, 2010
Non-patent document 9: Biol. Pharm. Bull., 34, pp. 1348-1351, 2011

SUMMARY OF THE INVENTION

Object to be Achieved by the Invention

An object of the present invention is to provide a means for efficiently delivering an siRNA intracellularly into an immunocyte, especially dendritic cell having an antigen-presenting ability. More specifically, the object of the present invention is to provide a lipid membrane structure that can efficiently deliver an siRNA intracellularly into an immunocyte such as dendritic cell, and a novel compound useful for the manufacture of the lipid membrane structure.

Means for Achieving the Object

In order to realize efficient knockdown of a target gene in an immunocyte, especially dendritic cell, which has an antigen-presenting ability, the inventors of the present invention conducted various researches concerning means for efficiently delivering siRNA into cells. As a result, they found that if a lipid membrane structure such as MEND is formed by using a lipid compound having two unsaturated bonds in two aliphatic acid chains and showing a high pKa due to extended carbon chains in the hydrophilic parts, extremely high endosomal escaping property thereof can be attained, and knockdown of a target gene with siRNA can be very efficiently performed with the lipid membrane structure prepared with a lipid composition containing such a lipid compound as mentioned above. It was also found that, in dendritic cells in which SOCS1 has been knocked down by using this lipid membrane structure, marked enhancement of cytokine production is observed, and in mice administered with such dendritic cells, engraftment and growth of transplanted tumor are completely suppressed. The present invention was accomplished on the basis of the aforementioned findings.

The present invention thus provides a lipid compound represented by the following formula (I), or a salt thereof:

[Formula 1]

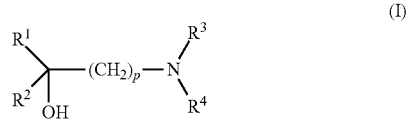

(I)

wherein, in the formula, $R^1$ and $R^2$ independently represent $CH_3-(CH_2)_n-CH=CH-CH_2-CH=CH-(CH_2)_m-$ (n represents an integer of 3 to 5, and m represents an integer of 6 to 10), p represents an integer of 2 to 7, and $R^3$ and $R^4$ independently represent a $C_{1-4}$ alkyl group or a $C_{2-4}$ alkenyl group.

According to preferred embodiments of the aforementioned invention, there are provided the aforementioned lipid compound or a salt thereof, wherein n is 4, m is an integer of 7 to 9, p is an integer of 3 to 5, and $R^3$ and $R^4$ are independently $C_{1-4}$ alkyl groups; the aforementioned lipid compound or a salt thereof, wherein $R^1$ and $R^2$ are the same, n is 4, m is an integer of 7 to 9, p is 4, and $R^3$ and $R^4$ are independently methyl group or ethyl group; and the aforementioned lipid compound or a salt thereof, wherein $R^1$ and $R^2$ are the same, n is 4, m is 8, p is 4, and $R^3$ and $R^4$ are methyl groups.

As another aspect of the present invention, there is provided a lipid compound represented by the aforementioned formula (I) or a salt thereof, which is for use as a lipid component of a lipid membrane structure for delivering an siRNA intracellularly into a cell. According to preferred embodiments of this invention, there are provided the aforementioned lipid compound, wherein the cell is an immunocyte, preferably a dendritic cell; the aforementioned lipid compound or a salt thereof, wherein the lipid membrane structure is a liposome; and the aforementioned lipid compound or a salt thereof, which is a multi-functional envelope-type nano device (MEND).

As a still further aspect of the present invention, there is provided a lipid membrane structure for delivering an siRNA intracellularly into a cell, which encapsulates the siRNA inside thereof, and contains a lipid compound represented by the aforementioned formula (I) as a lipid component. This lipid membrane structure can be used for knocking down a target gene in a dendritic cell, which has an antigen-presenting ability. Therefore, in view of the above, the present invention also provides the aforementioned lipid membrane structure, which is for use in knockdown of a target gene in a dendritic cell.

According to preferred embodiments of the aforementioned invention, there are provided the aforementioned lipid membrane structure, which contains the aforementioned lipid compound, wherein n is 4, m is an integer of 7 to 9, p is an integer of 3 to 5, and $R^3$ and $R^4$ are independently $C_{1-4}$ alkyl groups; the aforementioned lipid membrane structure, which contains the aforementioned lipid compound, wherein $R^1$ and $R^2$ are the same, n is 4, m is an integer of 7 to 9, p is 4, and $R^3$ and $R^4$ are independently methyl group or ethyl group; and the aforementioned lipid membrane structure, which contains the aforementioned lipid compound, wherein $R^1$ and $R^2$ are the same, n is 4, m is 8, p is 4, and $R^3$ and $R^4$ are methyl groups.

According to further preferred embodiments, there are provided the aforementioned lipid membrane structure, which contains one or more kinds of compounds selected from the group consisting of a lipid compound of the aforementioned formula (I), 1-palmitoyl-2-oleyl-sn-glycero-3-phosphoethanolamine (POPE), cholesterol (Chol), 1,2-dimyristoyl-sn-glycerol, and methoxy polyethylene glycol 2000 (PEG-DMG 2000) as lipid components; the aforementioned lipid membrane structure, which contains one or more kinds of compounds selected from the group consisting of a lipid compound of the aforementioned formula (I), cholesterol (Chol), 1,2-dimyristoyl-sn-glycerol, and methoxy polyethylene glycol 2000 (PEG-DMG 2000) as lipid components; the aforementioned lipid membrane structure, wherein the cell is an immunocyte, preferably a dendritic cell; the aforementioned lipid membrane structure, which is a liposome; and the aforementioned lipid membrane structure, which is a multi-functional envelope-type nano device (MEND).

The present invention also provides a method for delivering an siRNA intracellularly into a cell, preferably into an immunocyte, most preferably into a dendritic cell, which comprises the step of contacting the aforementioned lipid membrane structure encapsulating the siRNA inside thereof and containing a lipid compound represented by the aforementioned formula (I) as a lipid component with the cell. This method may be performed in a living body of a mammal including human, or may be performed in vitro by using a cell separated and collected from a living body.

For example, when dendritic cells are used, a dendritic cell therapy can be performed by introducing an siRNA into dendritic cells separated and collected from a patient according to the aforementioned method, and then administering the dendritic cells in which the target gene has been knocked down to the patient. Therefore, according to the present invention, there is provided a method for immunotherapy, which comprises separating and collecting a dendritic cell from a patient, introducing an siRNA intracellularly into the dendritic cell in vitro, and administering the dendritic cell in which a target gene has been knocked down to the patient. The present invention also provides the aforementioned lipid membrane structure, which is used in an immunotherapy comprising separating and collecting a dendritic cell from a patient, introducing an siRNA intracellularly into the dendritic cell in vitro, and then administering the dendritic cell in which a target gene has been knocked down to the patient, for knocking down the target gene in the dendritic cell.

Effect of the Invention

The lipid membrane structure provided by the present invention can efficiently migrate intracellularly into an arbitrary cell such as immunocytes including dendritic cell, into which it is difficult to introduce an siRNA, and can efficiently escape from endosome. Therefore, it can efficiently release the encapsulated siRNA intracellularly, and knock out a target gene with the siRNA. Accordingly, by using the lipid membrane structure of the present invention, an effective immunotherapy, preferably a dendritic cell therapy, which utilizes an siRNA, can be performed in, for example, a cancer therapy. Further, if a lipid membrane structure such as liposome is prepared by using the lipid compound provided by the present invention as a lipid component, extremely high endosomal escaping property thereof can be attained, and efficient delivery of an siRNA, from the lipid membrane structure containing the lipid compound, into the cytoplasm is achievable.

MODES FOR CARRYING OUT THE INVENTION

Figure 1:
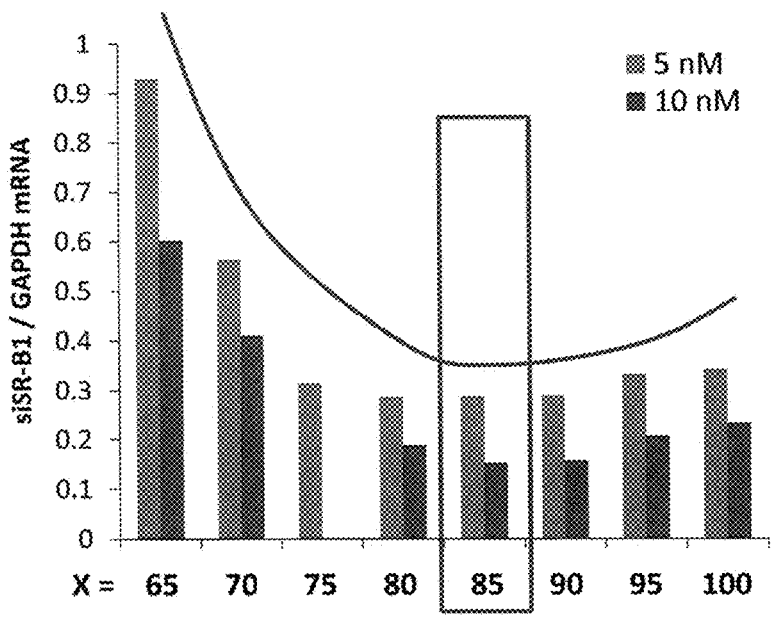
FIG. 1 A graph showing the results of acquisition of knockdown efficiency, in which ratio of YSK12 in a lipid composition of YSK12/POPE/Chol was changed with 2 mol % of DMG-PEG 2000 at an siRNA concentration of 5 nM or 10 nM for optimization of YSK12-MEND.

In the formula (I), $R^1$ and $R^2$ independently represent $CH_3—(CH_2)_n—CH=CH—CH_2—CH=CH—(CH_2)_m—$. n represents an integer of 3 to 5, and m represents an integer of 6 to 10. Preferably, n is 4, and m is an integer of 7 to 9. Particularly preferably, n is 4, and m is 8. Although $R^1$ and $R^2$ may be the same or different, it is preferred that they are the same groups. p represents an integer of 2 to 7, preferably an integer of 3 to 5, particularly preferably 4. $R^3$ and $R^4$ independently represent a $C_{1-4}$ alkyl group or a $C_{2-4}$ alkenyl group. It is preferred that they are independently $C_{1-4}$ alkyl groups, it is more preferred that $R^3$ and $R^4$ are independently methyl group or ethyl group, and it is particularly preferred that $R^3$ and $R^4$ are methyl groups.

The lipid compounds represented by formula (I) may exist as an acid addition salt. Type of acid that constitutes the salt is not particularly limited, and may be a mineral acid or organic acid. Examples include, for example, mineral acid salts such as hydrochloride, nitrate, and sulfate, and organic acid salt such as tartrate, oxalate, maleate, malate, p-toluenesulfonate, and methanesulfonate, but are not necessarily limited to these. There may be a hydrate or solvate of the lipid compounds represented by formula (I) or a salt thereof, and these substances are also fall within the scope of the present invention. For the compounds wherein $R^1$ and $R^2$ are different, there may be optical isomers. Pure optical isomers, arbitrary mixtures of optical isomers, racemates, and the like also fall within the scope of the present invention.

A preparation method of the lipid compound of the formula (I) wherein $R^1$ and $R^2$ are the same, n is 4, m is 8, and $R^3$ and $R^4$ are methyl groups as a particularly preferred compound among the compounds of the formula (I) (this compound may be referred to as "YSK12" in this specification) is specifically shown in the section of Examples of this specification. With reference to the preparation method described in the examples, those skilled in the art can easily prepare arbitrary compounds of the formula (I) by appropriately choosing starting compounds, reagents, reaction conditions, and the like. In addition, pKa of the compounds of the formula (I) is about 7.8 to 8.2, preferably about 8.0.

Examples of lipids constituting the lipid membrane structure of the present invention include, for example, phospholipids, glycolipids, sterols, saturated or unsaturated fatty acids, and the like.

Examples of the phospholipids and phospholipid derivatives include, for example, phosphatidylethanolamine, phosphatidylcholine, phosphatidylserine, phosphatidylinositol, phosphatidylglycerol, cardiolipin, sphingomyelin, ceramide phosphorylethanolamine, ceramide phosphorylglycerol, ceramide phosphorylglycerol phosphate, 1,2-dimyristoyl-1,2-deoxyphosphatidylcholine, plasmalogen, phosphatidic acid, and the like, and one or more kinds of these can used independently or in combination. Although the fatty acid residues of these phospholipids are not particularly limited, examples include saturated or unsaturated aliphatic acid residues having 12 to 20 carbon atoms, and specific examples include, for example, acyl groups derived from such a fatty acid as lauric acid, myristic acid, palmitic acid, stearic acid, oleic acid, and linoleic acid. Further, a phospholipid derived from a natural product such as egg yolk lecithin and soybean lecithin can also be used.

Examples of the glycolipids include, for example, glyceroglycolipids (for example, sulfoxyribosyl glyceride, diglycosyl diglyceride, digalactosyl diglyceride, galactosyl diglyceride, and glycosyl diglyceride), sphingoglycolipids (for example, galactosyl cerebroside, lactosyl cerebroside and ganglioside), and the like.

Examples of the sterols include, for example, animal-derived sterols (for example, cholesterol, cholesterol succinate, lanosterol, dihydrolanosterol, desmosterol and dihydrocholesterol), plant-derived sterols (phytosterol) (for example, stigmasterol, sitosterol, campesterol and brassicasterol), microorganism-derived sterols (for example, thymosterol and ergosterol), and the like.

Examples of the saturated or unsaturated fatty acids include, for example, saturated or unsaturated fatty acids having 12 to 20 carbon atoms, such as palmitic acid, oleic acid, stearic acid, arachidonic acid, and myristic acid.

Form of the lipid membrane structure is not particularly limited, and examples of the form in which lipid membrane structures are dispersed in an aqueous solvent include uni-lamella liposomes, multi-lamella liposomes, O/W type emulsions, W/O/W type emulsions, spherical micelles, fibrous micelles, layered structures of irregular shapes and the like. Examples of preferred form of the lipid membrane structure of the present invention include liposomes. Although liposomes may be explained hereafter as a preferred embodiment of the lipid membrane structure of the present invention, the lipid membrane structure of the present invention is not limited to liposomes.

The lipid membrane structure of the present invention is a lipid membrane structure for delivering an siRNA intracellularly into a cell, and is characterized by encapsulating an siRNA inside thereof and containing a lipid compound represented by the aforementioned formula (I) as a lipid component. Although type of cell into which siRNA should be delivered with the lipid membrane structure of the present invention is not particularly limited, preferred examples include immunocytes, and particularly preferred examples include dendritic cell.

siRNA (small interfering RNA) is a low molecular weight double-stranded RNA comprising 21 to 23 base pairs, and it participates in the RNA interference (RNAi) and suppresses gene expression in a sequence-specific manner by disrupting mRNA. It has been reported that a synthesized siRNA causes RNA interference in a human cell, and a gene can be knocked down by the RNA interference using siRNA. Therefore, use thereof as a medicament and application thereof in the field of cancer treatment are expected. Type of siRNA usable in the present invention is not particularly limited, and any siRNA that can cause RNA interference may be used. However, RNA having a structure of a double-stranded RNA of 21 to 23 base pairs in which 2 nucleotides of the 3' end portion of the RNA chain protrude, and each chain has phosphate group at the 5' end and hydroxyl group at the 3' end can generally be used as the siRNA used in the present invention. An siRNA in which the hydroxyl group at the position 2' of the ribose structure is replaced with methoxy group, fluoro group, or methoxyethyl group, and the phosphodiester bond is partially replaced with a phosphorothioate bond can also be used.

By using the lipid membrane structure of the present invention, an siRNA can be delivered intracellularly into a cell, preferably into an immunocyte, and most preferably into a dendritic cell. Although this method can also be performed in a living body of a mammal including human, it may also be performed in vitro by using a cell separated and extracted from a living body. For example, in the case of using a dendritic cell, a dendritic cell therapy can be performed by introducing an siRNA into dendritic cells separated and collected from a patient, and then administering the dendritic cells in which the target gene has been knocked down to the patient. Although it is not intended to be bound by any specific theory, a double-stranded siRNA delivered intracellularly into a cell by the lipid membrane structure of the present invention is dissociated into single strands by the action of the enzyme called helicase, the strands form a complex (RISC) with an Argonaute protein that shows the endonuclease activity to a target mRNA, or the like, and thus a target gene can be knocked down by RNA interference.

Although the lipid compound of the formula (I) may be used alone as the lipid component of the lipid membrane structure of the present invention, it is generally preferable to form the lipid membrane structure with a combination of one or more kinds of the lipids explained above and a lipid compound of the formula (I). Although the combination of two or more kinds of lipids and mixing ratio thereof are not particularly limited, types of lipids to be used and mixing ratio thereof can be optimized on the basis of, for example, knockdown activity against a target gene or the like as an index, as specifically described in the examples. For example, as for the combination of a compound of the formula (I), 1-palmitoyl-2-oleyl-sn-glycero-3-phosphoethanolamine (POPE), cholesterol (Chol), 1,2-dimyristoyl-sn-glycerol, and methoxy polyethylene glycol 2000 (PEG-DMG 2000) as lipid components, the knockdown activity can be increased with 80 to 90%, preferably about 85%, of the compound of the formula (I), and about 1 to 2%, preferably about 1%, of PEG-DMG 2000, as the content ratios, and/or, when the content ratio of the compound of the formula (I) is 85%, with a ratio of POPE/Chol of about 0/15 to 4/11, preferably 0/15. However, the present invention is not limited by use of these specific lipids and mixing ratios thereof.

Although particle size of the lipid membrane structure of the present invention is not particularly limited, it is, for example, about 120 to 300 nm, preferably about 150 to 250 nm, more preferably about 180 nm. The polydispersity index (PDI) is about 0.05 to 0.1, preferably about 0.06 to 0.08, more preferably about 0.07. The zeta potential can be in the range of 5.5 to 6.0 mV, preferably about 5.8 mV.

The lipid membrane structure of the present invention may be subjected to an appropriate surface modification or the like as required.

For example, in order to promote migration intracellularly into nuclei of the lipid membrane structure of the present invention, surface of the lipid membrane structure can also be modified with, for example, a tri- or higher oligosaccharide compound. Although type of the tri- or higher oligosaccharide compound is not particularly limited, for example, an oligosaccharide compound comprising about 3 to 10 of linked saccharide units can be used, and an oligosaccharide compound comprising about 3 to 6 of linked saccharide units can be preferably used.

More specifically, examples of the oligosaccharide compound include, for example, trisaccharide compounds such as cellotriose (β-D-glucopyranosyl-(1->4)-β-D-glucopyranosyl-(1->4)-D-glucose), chacotriose (α-L-rhamnopyranosyl-(1->2)-[α-L-rhamnopyranosyl-(1->4)]-D-glucose), gentianose (β-D-fructofuranosyl-β-D-glucopyranosyl-(1->6)-α-D-glucopyranoside), isomaltotriose (α-D-glucopyranosyl-(1->6)-α-D-glucopyranosyl-(1->6)-D-glucose), isopanose (α-D-glucopyranosyl-(1->4)-[α-D-glucopyranosyl-(1->6)]-D-glucose), maltotriose (α-D-glucopyranosyl-(1->4)-α-D-glucopyranosyl-(1->4)-D-glucose), manninotriose (α-D-galactopyranosyl-(1->6)-α-D-galactopyranosyl-(1->6)-D-glucose), melezitose (α-D-glucopyranosyl-(1->3)-β-D-fructofuranosyl=α-D-glucopyranoside), panose (α-D-glucopyranosyl-(1->6)-α-D-glucopyranosyl-(1->4)-D-glucose), planteose (α-D-galactopyranosyl-(1->6)-β-D-fructofuranosyl=α-D-glucopyranoside), raffinose (β-D-fructofuranosyl=α-D-galactopyranosyl-(1->6)-α-D-glucopyranoside), solatriose (α-L-rhamnopyranosyl-(1->2)-[β-D-glucopyranosyl-(1->3)]-D-galactose), and umbelliferose (β-D-fructofuranosyl=α-D-galactopyranosyl-(1->2)-α-D-galactopyranoside; tetrasaccharide compounds such as lycotetraose (β-D-glucopyranosyl-(1->2)-[β-D-xylopyranosyl-(1->3)]-β-D-glucopyranosyl-(1->4)-β-D-galactose, maltotetraose (α-D-glucopyranosyl-(1->4)-α-D-glucopyranosyl-(1->4)-α-D-glucopyranosyl-(1->4)-D-glucose), and stachyose (β-D-fructofuranosyl=α-D-galactopyranosyl-(1->6)-α-D-galactopyranosyl-(1->6)-α-D-glucopyranoside); pentasaccharide compounds such as maltopentaose (α-D-glucopyranosyl-(1->4)-α-D-glucopyranosyl-(1->4)-α-D-glucopyranosyl-(1->4)-α-D-glucopyranosyl-(1->4)-D-glucose), and verbascose (β-D-fructofuranosyl-α-D-galactopyranosyl-(1->6)-α-D-galactopyranosyl-(1->6)-α-D-galactopyranosyl-(1->6)-α-D-glucopyranoside); and hexasaccharide compounds such as maltohexaose (α-D-glucopyranosyl-(1->4)-α-D-glucopyranosyl-(1->4)-α-D-glucopyranosyl-(1->4)-α-D-glucopyranosyl-(1->4)-α-D-glucopyranosyl-(1->4)-D-glucose), but the oligosaccharide compound is not limited to these.

Oligosaccharide compounds as trimer to hexamer of glucose can be preferably used, and oligosaccharide compounds as trimer or tetramer of glucose can be more preferably used. More specifically, isomaltotriose, isopanose, maltotriose, maltotetraose, maltopentaose, maltohexaose, and the like can be preferably used, and among these, maltotriose, maltotetraose, maltopentaose, and maltohexaose consisting of glucose units linked through al-4 linkages are more preferred. Particularly preferred are maltotriose and maltotetraose, and most preferred is maltotriose. Although amount of the oligosaccharide compound used for the surface modification of the lipid membrane structure is not particularly limited, it is, for example, about 1 to 30 mol %, preferably about 2 to 20 mol %, more preferably about 5 to 10 mol %, based on the total amount of lipids.

Although the method for modifying the surface of the lipid membrane structure with the oligosaccharide compound is not particularly limited, for example, since liposomes consisting of lipid membrane structures of which surfaces are modified with monosaccharides such as galactose and mannose are known (International Patent Publication WO2007/102481), the surface modification method described in this publication can be employed. The entire disclosure of the aforementioned publication is incorporated into the disclosure of this specification by reference. This means is a method of binding a monosaccharide compound to polyalkylene glycolated lipids to perform surface modification of lipid membrane structures. Since surfaces of lipid membrane structures can be simultaneously modified with polyalkylene glycol by this means, it is preferred.

Stability such as blood retainability of a liposome can be enhanced by modifying the surface of the lipid membrane structure as the liposome with a hydrophilic polymer such as polyalkylene glycol. This means is described in, for example, Japanese Patent Unexamined Publication (KOKAI) Nos. 1-249717, 2-149512, 4-346918, 2004-10481, and the like. As the hydrophilic polymer, a polyalkylene glycol is preferred. As the polyalkylene glycol, for example, polyethylene glycol, polypropylene glycol, polytetramethylene glycol, polyhexamethylene glycol, and the like can be used. Molecular weight of the polyalkylene glycol is, for example, about 300 to 10,000, preferably about 500 to 10,000, more preferably about 1,000 to 5,000.

The surface modification of the lipid membrane structure with a polyalkylene glycol can be easily performed by constructing the lipid membrane structure using, for example, a polyalkylene glycol-modified lipid as a lipid membrane-constituting lipid. For example, when the modification with a polyethylene glycol is performed, stearylated polyethylene glycols (for example, PEG45 stearate (STR-PEG45) and the like) can be used. In addition, polyethylene glycol derivatives, such as N-{carbonyl-methoxypolyethylene glycol 2000}-1,2-dipalmitoyl-sn-glycero-3-phosphoethanolamine, n-{carbonyl-methoxypolyethylene glycol 5000}-1,2-dipalmitoyl-sn-glycero-3-phosphoethanolamine, N-{carbonyl-methoxypolyethylene glycol 750}-1,2-distearoyl-sn-glycero-3-phosphoethanolamine, N-{carbonyl-methoxypolyethylene glycol 2000}-1,2-distearoyl-sn-glycero-3-phosphoethanolamine, and N-(carbonyl-methoxypolyethylene glycol 5000)-1,2-distearoyl-sn-glycero-3-phosphoethanolamine, can also be used. However, the polyalkylene glycolated lipid is not limited to these.

Further, by binding an oligosaccharide compound to the polyethylene glycol, surface modification with a polyalkylene glycol and surface modification with an oligosaccharide compound can also be simultaneously attained. However, the method for modifying the surface of the lipid membrane structure with a polyalkylene glycol or an oligosaccharide compound is not limited to the aforementioned method. For example, the surface modification may be performed by using a lipidated compound such as a stearylated polyalkylene glycol or oligosaccharide compound as a constituent lipid of the lipid membrane structure.

As lipid derivatives for enhancing retainability in blood used for the preparation of the lipid membrane structure of the present invention, for example, glycophorin, ganglioside GM1, phosphatidylinositol, ganglioside GM3, glucuronic acid derivative, glutamic acid derivative, polyglycerin-phospholipid derivative, and the like can also be used. As hydrophilic polymer for enhancing retainability in blood, besides polyalkylene glycol, dextran, pullulan, Ficoll, polyvinyl alcohol, styrene-maleic anhydride alternating copolymer, divinyl ether-maleic anhydride alternating copolymer, amylose, amylopectin, chitosan, mannan, cyclodextrin, pectin, carrageenan, and the like can also be used for the surface modification.

The lipid membrane structure of the present invention may contain one or two or more kinds of substances selected from the group consisting of a membrane stabilization agent such as sterol, glycerol, and a fatty acid ester thereof, an antioxidant such as tocopherol, propyl gallate, ascorbyl palmitate, and butylated hydroxytoluene, a chargeable substance, a membrane polypeptide, and the like. Examples of the chargeable substance that imparts positive charge include saturated or unsaturated fatty amines such as stearylamine and oleylamine; saturated or unsaturated synthetic cationic lipids such as dioleoyltrimethylammonium propane; cationic polymers, and the like, and examples of the chargeable substance that imparts negative charge include, for example, dicetyl phosphate, cholesteryl hemisuccinate, phosphatidylserine, phosphatidylinositol, phosphatidic acid, and the like. Examples of the membrane polypeptide include, for example, extrinsic membrane polypeptides, integral membrane polypeptides, and the like. Amounts of these substances to be added are not particularly limited, and can be appropriately chosen depending on the purpose.

Further, the lipid membrane structure of the present invention may be imparted with one or two or more functions selected from, for example, temperature change sensing function, membrane permeating function, gene expressing function, pH sensing function, and the like. By appropriately imparting these functions, retainability in blood of the lipid membrane structure encapsulating, for example, a nucleic acid containing a gene or the like can be improved, a rate of capture by reticuloendothelial systems of liver, spleen and the like can be reduced, the lipid membrane structure can be efficiently extricated from the endosome and transferred to the nucleus after endocytosis of a target cell, and it becomes possible to attain high gene expression activity in the nucleus.

Examples of temperature change-sensitive lipid derivatives that can impart the temperature change sensing function include, for example, dipalmitoylphosphatidylcholine and the like. Examples of pH-sensitive lipid derivatives that can impart the pH sensing function include, for example, dioleoylphosphatidylethanolamine and the like.

Further, the lipid membrane structure of the present invention may also be modified with a substance that can specifically bind with a receptor or antigen on the surface of a cell, such as antibodies, to improve efficiency of delivery of a substance into the nucleus. For example, a monoclonal antibody directed to a biological component specifically expressed in a target tissue or organ is preferably disposed on the surface of the lipid membrane structure. This technique is described in, for example, STEALTH LIPOSOME (pages 233 to 244, published by CRC Press, Inc., edited by Danilo Lasic and Frank Martin) and the like. As a component of the lipid membrane structure, there can be contained a lipid derivative that can react with mercapto group in a monoclonal antibody or a fragment thereof (e.g., Fab fragment, F(ab')$_2$ fragment, Fab' fragment and the like), specifically, a lipid derivative having a maleinimide structure such as poly(ethylene glycol)-α-distearoylphosphatidylethanolamine-ω-maleinimide and α-[N-(1,2-distearoyl-an-glycero-3-phosphorylethyl)carbamyl]-ω-{3-[2-(2,5-di-hydro-2,5-dioxo-1H-pyrrol-1-yl)ethanecarboxamido] propyl}-poly(oxy-1,2-ethanediyl), and thereby the monoclonal antibody can be bound to the surface of the membrane of the lipid membrane structure.

Surface of the lipid membrane structure of the present invention may be modified with a polypeptide containing a plurality of contiguous arginine residues (henceforth referred to as "polyarginine"). As the polyarginine, preferably a polypeptide containing 4 to 20 contiguous arginine residues, more preferably a polypeptide consisting only of 4 to 20 contiguous arginine residues, most preferably octaarginine, and the like can be used. By modifying the surface of a lipid membrane structure such as liposome with a polyarginine such as octaarginine, intracellular delivery efficiency of a target substance encapsulated in liposome can be improved (Journal of Controlled Release, 98, pp. 317-323, 2004; International Patent Publication WO2005/32593). Surface of the lipid membrane structure can be easily modified with a polyarginine according to the method described in the aforementioned publications using, for example, a lipid-modified polyarginine such as stearylated octaarginine as a constituent lipid of the lipid membrane structure. The disclosures of the aforementioned publications and the disclosures of all of the references cited in the publications are incorporated into the disclosure of this specification by reference.

When an siRNA is encapsulated in the lipid membrane structure of the present invention, a compound having a nucleic acid-introducing function can also be added. Examples of such a compound include, for example, O,O'—N-didodecanoyl-N-(α-trimethylammonioacetyl)-diethanolamine chloride, O,O'—N-ditetradecanoyl-N-(α-trimethylammonioacetyl)-diethanolamine chloride, O,O'—N-dihexadecanoyl-N-(α-trimethylammonioacetyl)-diethanolamine chloride, O,O'—N-dioctadecenoyl-N-(α-trimethylammonioacetyl)-diethanolamine chloride, O,O', O''-tridecanoyl-N-(ω-trimethylammoniodecanoyl) aminomethane bromide, N-[α-trimethylammonioacetyl]-didodecyl-D-glutamate, dimethyldioctadecylammonium bromide, 2,3-dioleyloxy-N-[2-(sperminecarboxamido) ethyl]-N,N-dimethyl-1-propane ammonium trifluoroacetate, 1,2-dimyristyloxypropyl-3-dimethyl-hydroxyethylammonium bromide, 3-β-[N—(N',N'-dimethylaminoethane)carbamoyl]cholesterol, and the like. These compounds having a nucleic acid-introducing function may be disposed at an arbitrary position of the membrane of the lipid membrane structure, and/or filled in the inside of the lipid membrane structure.

A multifunctional envelope-type nano device (MEND) is known, and it can be preferably used as the lipid membrane structure of the present invention. As MEND, there has been reported, for example, one having a structure that it contains a complex of a nucleic acid such as plasmid DNA and a cationic polymer such as protamine as a core, and the core is encapsulated in the inside of a lipid envelope membrane in the form of liposome. It has also been reported that, on the lipid envelope membrane of MEND, a peptide for adjusting pH responding property and membrane permeability can be disposed as required, and the external surface of the lipid envelope membrane can be modified with an alkylene glycol such as polyethylene glycol. There is also known MEND in which condensed DNA and the cationic polymer are encapsulated inside of the lipid envelope of MEND, which is designed so that efficient gene expression can be attained. As for MEND, for example, references for general remarks, such as Drug Delivery System, 22-2, pp. 115-122, 2007, can be referred to. The disclosure of the aforementioned publication and the disclosures of all of the references cited in this publication are incorporated into the disclosure of this specification by reference.

Although form of the lipid membrane structure is not particularly limited, examples include, for example, a dispersion in an aqueous solvent (for example, water, physiological saline, phosphate buffered physiological saline, and the like), a lyophilized product of the aqueous dispersion, and the like.

The method for preparing the lipid membrane structure is not particularly limited, either, and an arbitrary method available for those skilled in the art can be employed. For example, the lipid membrane structure can be prepared by dissolving all the lipid components in an organic solvent such as chloroform, forming a lipid membrane by exsiccation under reduced pressure in an evaporator or spray drying using a spray dryer, then adding an aqueous solvent to the aforementioned dried mixture, and emulsifying the mixture with an emulsifier such as homogenizer, an ultrasonic emulsifier, a high pressure injection emulsifier, or the like. Further, it can be prepared by a method well known as a method for preparing liposomes, for example, the reverse phase evaporation method, and the like. When it is desired to control the size of the lipid membrane structure, extrusion (extrusion filtration) can be performed under high pressure by using a membrane filter having pores of uniform diameters, or the like. Although size of the dispersed lipid membrane structure is not particularly limited, in the case of liposome, for example, particle size is about 50 nm to 5 μm, preferably about 50 nm to 400 nm, more preferably 50 nm to 300 nm, still more preferably 150 nm to 250 nm. The particle size can be measured by, for example, the DLS (dynamic light scattering) method.

The composition of the aqueous solvent (dispersion medium) is not particularly limited, and examples include, for example, a buffer such as phosphate buffer, citrate buffer, and phosphate-buffered physiological saline, physiological saline, a medium for cell culture and the like. Although the lipid membrane structure can be stably dispersed in these aqueous solvents (dispersion media), the solvents may be further added with a saccharide (aqueous solution), for example, a monosaccharide such as glucose, galactose, mannose, fructose, inositol, ribose and xylose, a disaccharide such as lactose, sucrose, cellobiose, trehalose and maltose, a trisaccharide such as raffinose and melezitose, a polysaccharide such as cyclodextrin, a sugar alcohol such as erythritol, xylitol, sorbitol, mannitol, and maltitol, and the like, or a polyhydric alcohol (aqueous solution) such as glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol mono-alkyl ether and 1,3-butylene grycol. In order to stably store the lipid membrane structure dispersed in such an aqueous solvent for a long period of time, it is desirable to minimize electrolytes in the aqueous solvent from a viewpoint of physical stability such as prevention of aggregation. Further, from a viewpoint of chemical stability of lipids, it is desirable to control pH of the aqueous solvent to be in a range of from weakly acidic pH to around neutral pH (around pH 3.0 to 8.0), and/or to remove dissolved oxygen by nitrogen bubbling or the like.

When the resulting aqueous dispersion of the lipid membrane structure is lyophilized or spray-dried, use of a saccharide (aqueous solution), for example, a monosaccharide such as glucose, galactose, mannose, fructose, inositol, ribose and xylose, a disaccharide such as lactose, sucrose, cellobiose, trehalose and maltose, a trisaccharide such as raffinose and melezitose, a polysaccharide such as cyclodextrin, a sugar alcohol such as erythritol, xylitol, sorbitol, mannitol, and maltitol or the like may improve stability. When the aforementioned aqueous dispersion is frozen, use of the aforementioned saccharide or a polyhydric alcohol (aqueous solution) such as glycerin, diglycerin, polyglycerin, propylene glycol, polypropylene glycol, ethylene glycol, diethylene glycol, triethylene glycol, polyethylene glycol, ethylene glycol mono-alkyl ether, diethylene glycol mono-alkyl ether and 1,3-butylene glycol may improve stability.

In the inside of the lipid membrane structure of the present invention, for example, another substance can be encapsulated so long as the function of siRNA is not inhibited. Although type of the substance that can be encapsulated is not particularly limited, active ingredients of arbitrary medicaments such as antitumor agent, anti-inflammatory agent, antimicrobial agent, and antiviral agent as well as other arbitrary substances such as saccharides, peptides, nucleic acids, low molecular weight compounds, and metallic compounds can be encapsulated. Examples of the nucleic acid include a nucleic acid containing a gene, and specific examples include, for example, a gene incorporated into a plasmid. However, the nucleic acid is not limited to these specific examples.

EXAMPLES

Hereafter, the present invention will be more specifically explained with reference to examples. However, the scope of the present invention is not limited to the following examples.

Example 1: Synthesis of YSK12

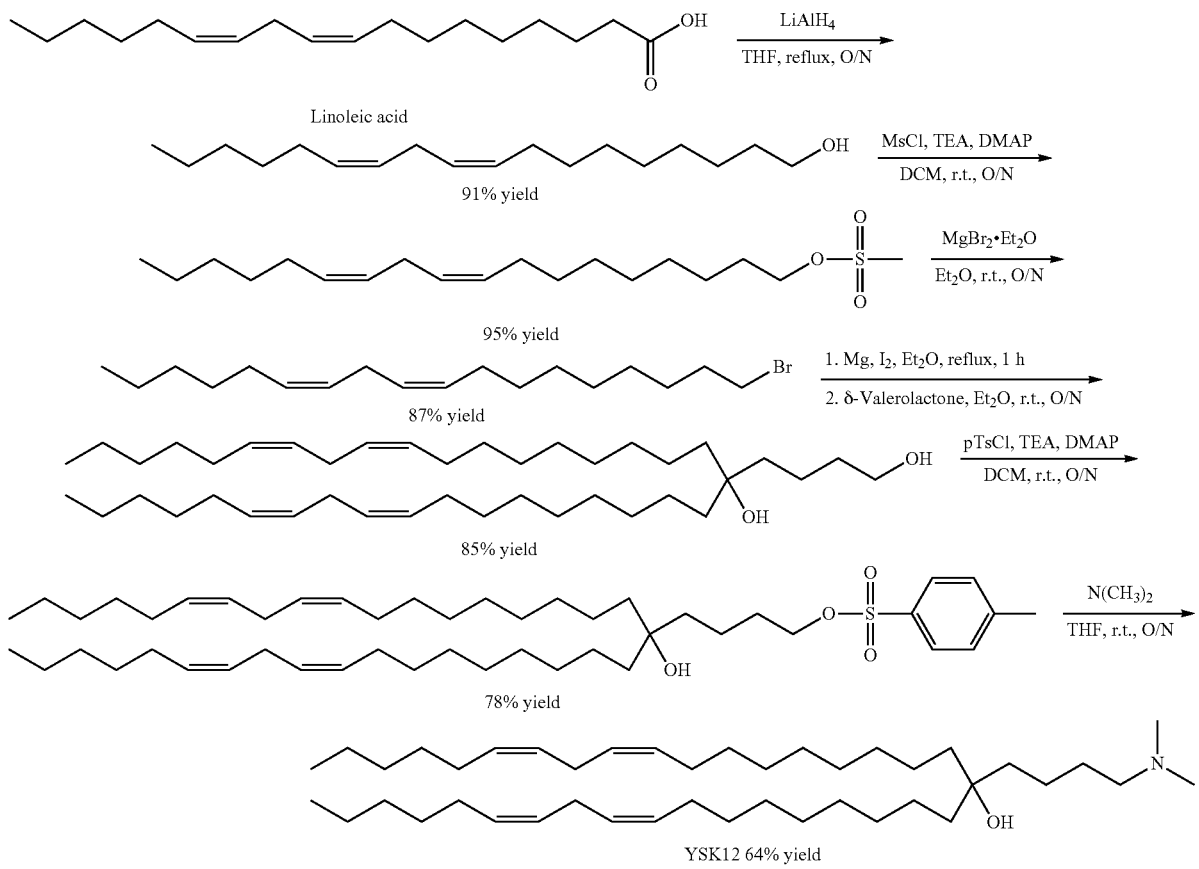

[Formula 2]

According to the scheme mentioned above, YSK12 was synthesized from linoleic acid.

(1) (9z,12z)-Octadecadien-1-ol

Lithium aluminum hydride (2.73 g, 72 mmol) was suspended in tetrahydrofuran (THF, 190 mL) cooled at 4° C. Linoleic acid (10 g, 36 mmol) was added dropwise to the suspension, and the resulting mixture was stirred for 10 minutes. Then, the mixture was refluxed overnight with heating on an oil bath. After cooling the mixture, 1 mol/L aqueous sodium hydroxide (100 mL) was added to terminate the reaction. Then, the reaction mixture was diluted with ethyl acetate (100 mL), and filtered, and the filtrate was washed with saturated aqueous sodium hydrogencarbonate. Then, the organic layer was collected, and dried over anhydrous sodium sulfate. The organic layer was filtered, and the solvent was evaporated by using a rotating evaporator to obtain a crude product. The crude product was purified by silica gel chromatography (elution solvent, hexane:ethyl acetate, continuous gradient) to obtain 9z,12z-octadecadien-1-ol (8.68 g, 32.6 mmol) as colorless oil. Yield was 91%.

Proton nuclear magnetic resonance ($^1$H NMR, 500 MHz) data of 9z,12z-octadecadien-1-ol $\delta$=0.88 (t, 3H), 1.25-1.36 (m, 16H), 1.53-1.58 (m, 2H), 2.02-2.06 (m, 4H), 2.76 (t, 2H), 3.62 (t, 2H), 5.29-5.40 (m, 4H)

(2) (9z,12z)-Octadecadien-1-methanesulfonate (9z,12z)-Octadecadien-1-ol (8.68 g, 32.6 mmol) was dissolved in dichloromethane (100 mL), and N,N-dimethyl-4-aminopyridine (DMAP, 366 mg, 3.26 mmol) and triethylamine (TEA, 6.8 mL, 48.9 mmol) were added to the solution. Then, methanesulfonyl chloride (3.03 mL, 39.1 mmol) diluted with dichloromethane (50 mL) was added dropwise to the mixture by using a dropping funnel, and the resulting mixture was stirred overnight at room temperature. The reaction mixture was collected, and washed with saturated aqueous sodium hydrogencarbonate. Then, anhydrous sodium sulfate was added to the organic layer for dehydration. The organic layer was filtered, and the solvent was evaporated by using a rotating evaporator to obtain a crude product. The crude product was purified by silica gel chromatography {elution solvent, hexane:ethyl acetate (continuous gradient) to obtain (9z,12z)-octadecadien-1-methanesulfonate (10.64 g, 30.9 mmol) as colorless oil. Yield was 95%.

Proton nuclear magnetic resonance ($^1$H NMR, 500 MHz) data of 9z,12z-octadecadien-1-methanesulfonate $\delta$=0.88 (t, 3H), 1.06-1.18 (m, 18H), 1.70-1.90 (m, 2H), 2.00-2.19 (m, 4H), 2.79 (t, 2H), 3.06 (s, 3H), 4.20 (t, 2H), 5.21-5.42 (m, 4H)

(3) 18-Bromo-octadeca-(6z,9z)-diene (9z,12z)-Octadecadien-1-methanesulfonate (10.64 g) was dissolved in diethyl ether (140 mL), magnesium bromide ethyl etherate (16.0 g, 61.8 mmol) was added to the solution, and the resulting mixture was stirred overnight at room temperature. The reaction mixture was collected, and washed by using saturated aqueous sodium hydrogencarbonate (100 mL). Then, anhydrous sodium sulfate was added to the organic layer for dehydration. The organic layer was filtered, and the solvent was evaporated by using a rotating evaporator to obtain a crude product. The crude product was purified by silica gel chromatography {elution solvent, hexane:ethyl acetate (continuous gradient) to obtain 18-bromo-octadeca-(6z,9z)-diene (8.85 g, 26.9 mmol) as colorless oil. Yield was 87%.

Proton nuclear magnetic resonance ($^1$H NMR, 500 MHz) data of 18-bromo-octadeca-(6z,9z)-diene δ=0.88 (t, 3H), 1.27-1.46 (m, 18H), 1.80-1.88 (m, 2H), 2.00-2.09 (m, 4H), 2.77 (t, 2H), 3.40 (t, 2H), 4.20 (d, 2H), 5.29-5.41 (m, 4H)

(4) 4-[(9z, 12z)-Octadecadienyl]-(13z, 16z)-tricosadien-1,4-diol

18-Bromo-octadeca-(6z,9z)-diene (0.50 g, 1.52 mmol) was dissolved in diethyl ether (1.5 mL), magnesium shavings (609 mg, 25.1 mmol) were added to the solution, and then one broken piece of iodine was added to the solution. The mixture was left standing for 10 minutes at room temperature, and then stirred with heating at 45° C. on an oil bath, and 18-bromo-octadeca-(6z,9z)-diene (5.0 g, 15.2 mmol) dissolved in diethyl ether (6 mL) was added dropwise to the mixture. The reaction was allowed at 45° C. for 1 hour, and then the reaction mixture was cooled to room temperature. Then, 6-valerolactone (300 μL, 3.23 mmol) was added to the reaction mixture, and the reaction was allowed at room temperature for 1 hour. Then, the reaction mixture was cooled to 4° C., and filtered, and the filtrate was washed with saturated aqueous sodium hydrogencarbonate. Then, anhydrous sodium sulfate was added to the organic layer for dehydration. The organic layer was filtered, and the solvent was evaporated by using a rotating evaporator to obtain a crude product. The crude product was purified by silica gel chromatography {elution solvent, hexane:ethyl acetate (continuous gradient)} to obtain 4-[(9z, 12z)-octadecadienyl]-(13z, 16z)-tricosadien-1,4-diol (1.64 g, 2.73 mmol) as colorless oil. Yield from 6-valerolactone was 85%.

Proton nuclear magnetic resonance ($^1$H NMR, 500 MHz) data of 4-[(9z,12z)-octadecadienyl]-(13z,16z)-tricosadien-1,4-diol δ=0.88 (t, 6H), 1.25-1.1.46 (m, 46H), 2.02-2.06 (m, 8H), 2.77 (t, 4H), 3.66 (t, 2H), 5.30-5.40 (m, 8H)

(5) 4-[(9z,12z)-Octadecadienyl]-1-p-toluenesulfonyl-(13z,16z)-tricosadien-4-ol 4-[(9z,12z)-Octadecadienyl]-(13z, 16z)-tricosadien-1,4-diol (301 mg, 0.50 mmol) was dissolved in dichloromethane (5.0 mL), DMAP (6.11 mg, 0.05 mmol) and TEA 83.6 μL, 0.60 mmol) were added to the solution, p-toluenesulfonyl chloride (95.3 mg, 0.50 mmol) was successively added to the mixture, and the resulting mixture was stirred overnight at room temperature. Then, silica gel was added to the reaction mixture, and the solvent was evaporated by using a rotating evaporator. Then, the residue was purified by silica gel chromatography (elution solvent, hexane:ethyl acetate (continuous gradient) to obtain 293 mg (0.39 mmol) of the target compound as colorless oil. Yield was 78%.

Proton nuclear magnetic resonance ($^1$H NMR, 500 MHz) data of 4-[(9z,12z)-octadecadienyl]-1-p-toluenesulfonyl-(13z,16z)-tricosadien-4-ol δ=0.88 (t, 3H), 1.25-1.49 (m, 46H), 2.03-2.05 (m, 8H), 2.44 (s, 3H), 2.77 (t, 4H), 4.03 (t, 2H), 5.31-5.39 (m, 8H), 7.34 (d, 2H), 7.78 (d, 2H)

(6) 1-N,N-Dimethylamino-4-[(9z,12z)-octadecadienyl]-(13z, 16z)-tricosadien-4-ol A 2.0 M solution of dimethylamine in tetrahydrofuran (10 mL) was added to 293 mg (0.39 mmol) of the above-obtained compound, and the reaction was allowed overnight at room temperature. The solvent was evaporated by using a rotating evaporator, then dichloromethane (100 mL) was added to the residue, and the organic layer was washed with 0.1 M aqueous sodium hydroxide (100 mL). Then, anhydrous sodium sulfate was added to the organic layer for dehydration. The organic layer was filtered, and then the solvent was evaporated by using a rotating evaporator to obtain a crude product. The crude product was purified by silica gel chromatography (elution solvent, dichloromethane:methanol (continuous gradient) to obtain 155 mg (0.25 mmol) of the target compound as pale yellow oil. Yield was 64%.

Proton nuclear magnetic resonance ($^1$H NMR, 500 MHz) data of 1-N,N-dimethylamino-4-[(9z,12z)-octadecadienyl]-(13z,16z)-tricosadien-4-ol δ=0.87 (t, 6H), 1.23-1.40 (m, 46H), 2.02-2.07 (m, 8H), 2.26 (s, 6H), 2.33 (t, 2H), 2.77 (t, 4H), 5.31-5.39 (m, 8H)

Example 2: Preparation of YSK12-MEND

YSK12-MEND was prepared by the alcohol dilution method. To a solution containing YSK12, 1-palmitoyl-2-oleyl-sn-glycero-3-phosphoethanolamine (POPE), cholesterol (Chol), 1,2-dimyristoyl-sn-glycerol, and methoxy polyethylene glycol 2000 (DMG-PEG 2000) in a total lipid amount of 505 nmol in 90% t-butanol (400 μL), an aqueous solution (200 μL) containing siRNA (600 pmol) was added with stirring. A 20 mM citrate buffer (2 mL) was further added to the mixture with stirring, then PBS (3.5 ml) was added to the mixture, and then the resulting mixture was subjected to ultrafiltration.

Figure 2:
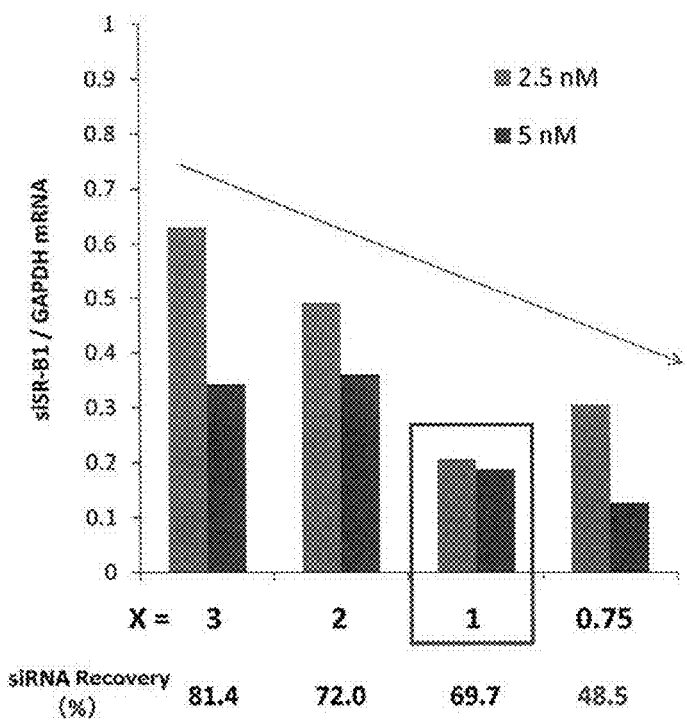
FIG. 2 A graph showing the results of acquisition of recovery ratio of siRNA, in which the DMG-PEG 2000 concentration was changed in the range of 3 to 0.75 mol % in a lipid composition of YSK12/POPE/Chol (85/7.5/7.5) at an siRNA concentration of 2.5 nM or 5 nM for optimization of YSK12-MEND.
Figure 3:
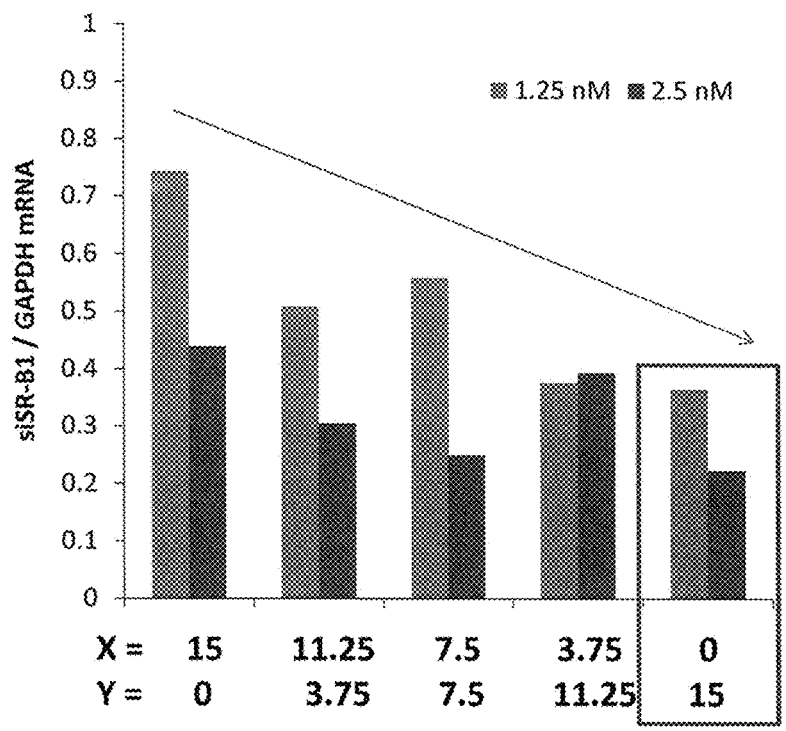
FIG. 3 A graph showing the results of acquisition of knockdown efficiency, in which ratio of POPE/Chol was changed in a lipid composition of YSK12/POPE/Chol with 85% of YSK12 and 1 mol % of DMG-PEG 2000 at an siRNA concentration of 1.25 nM or 2.5 nM for optimization of YSK12-MEND.

The lipid composition of YSK12-MEND was optimized by using mouse dendritic cells. Dendritic cells (6×10$^5$) were transfected with siRNA of which target is SR-B1 at an siRNA concentration of 5 nM or 10 nM in the absence of serum, a medium containing serum was added 2 hours thereafter, the cells were collected after 22 hours, and knockdown efficiency was evaluated (Warashina S. et al., Biol. Pharm. Bull., 34, pp. 1348-2351, 2011). The knockdown efficiency was evaluated by quantifying mRNA amount by real-time RT-PCR. As a result, it was found that the highest knockdown efficiencies were obtained at a YSK12 ratio of 85% (FIG. 1), DMG-PEG2000 ratio of 1% (FIG. 2), and POPC/Chol ratio of 0%/15% (FIG. 3). On the basis of these results, YSK12/Chol ratio was set to be 85/15, and DMG-PEG2000 concentration was set to be 1 mol % as the optimal composition. The optimized YSK12-MEND showed a particle size of 180±6 nm, polydispersity index (PDI) of 0.071±0.023, zeta-potential of 5.8±0.6 mV, and siRNA enclosing ratio (%) of 94.2±0.8.

Figure 4:
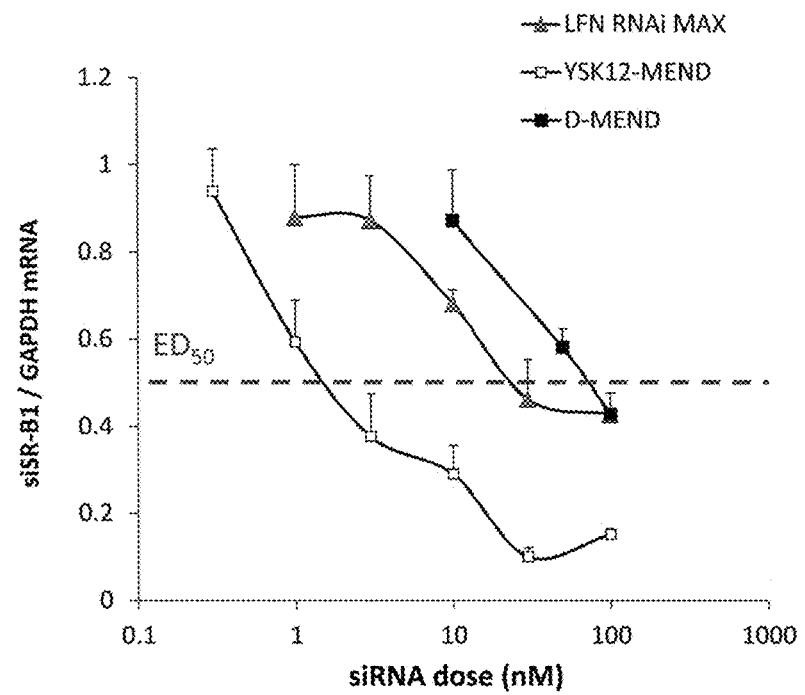
FIG. 4 A graph showing a dose/reaction curve of YSK12-MEND. As D-MEND, there was used one having the following characteristics: DOPE/PA=7:2; Chol-GALA, 1 mol %; and STR-R8, 10 mol %.
Figure 5:
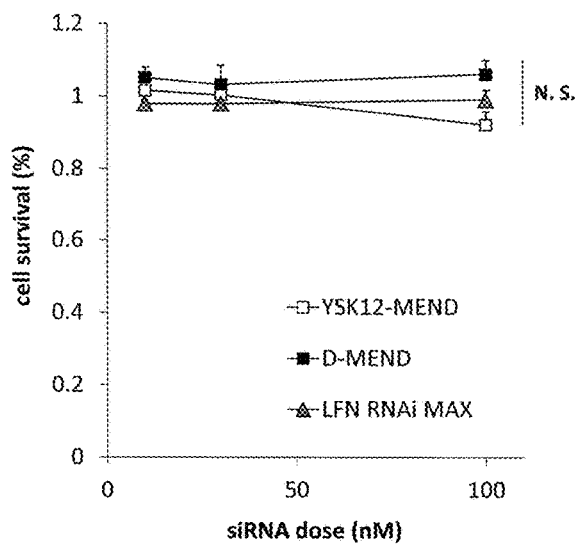
FIG. 5 A graph showing the results of evaluation of the cytotoxicity of YSK12-MEND FIG. 6 Photographs showing the results of evaluation of the endosomal escaping ability of YSK12-MEND. Light blue color indicates nuclei, green color indicates acid compartments, and red color indicates siRNA.

ED$_{50}$ of YSK12-MEND for the knockdown efficiency was compared with those of R8/GALA-D-MEND, which is a nano-carrier consisting of MEND of which envelope membrane number is controlled by modification with the octarginine (R8) peptide as a cell affinity device, and the GALA peptide as an endosomal escaping device (D-MEND, J. Control. Release, 143, pp. 311-317, 2010), and LFN RNAi MAX as a commercial reagent, which is considered to be a reagent that shows the highest knockdown efficiency among the commercial reagents. As a result, $ED_{50}$ of YSK12-MEND, D-MEND, and LFN RNAi MAX were 1.5 nM, 70 nM, and 25 nM, respectively, and thus YSK12-MEND showed a knockdown efficiency 47 times higher than that of D-MEND, and 17 times higher than that of LFN RNAi MAX (FIG. 4). Cytotoxicities of the regents were evaluated 2 hours after the transfection to the mouse dendritic cells by using the MTS assay. As a result, marked cytotoxicity was not observed with YSK12-MEND, D-MEND, and LFN RNAi MAX treatments (FIG. 5).

Figure 6:
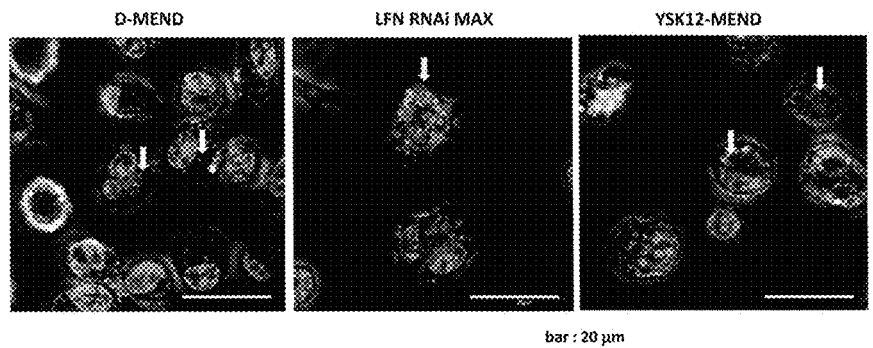
Figure 7:
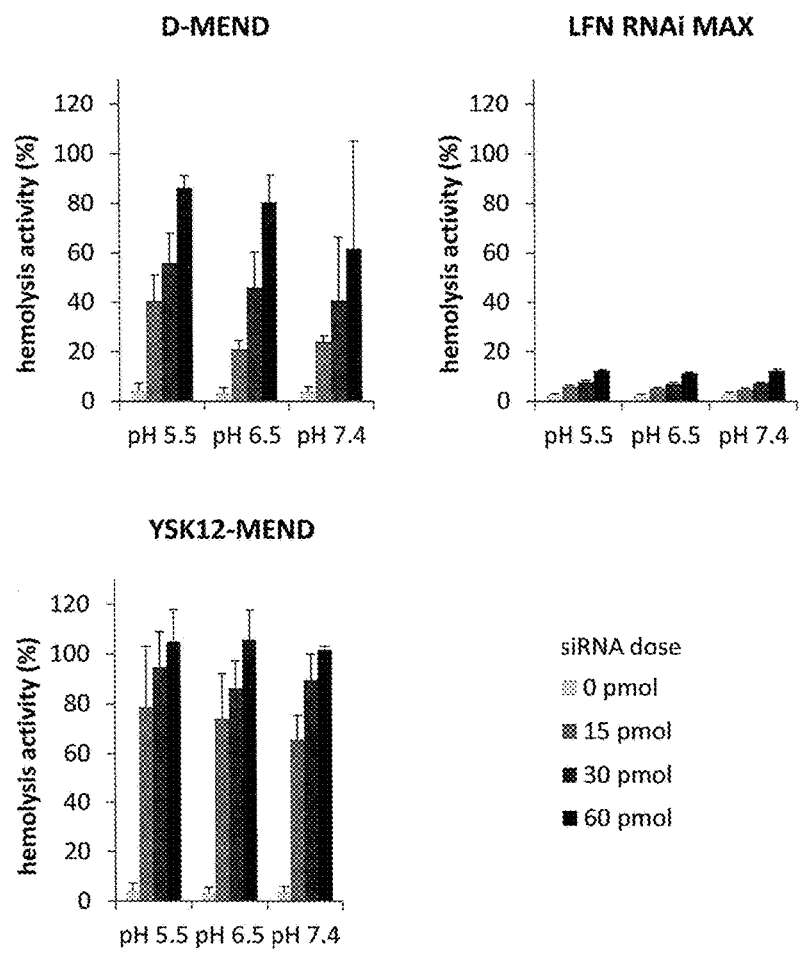
FIG. 7 Graphs showing the results of evaluation of the membrane-damaging action of YSK12-MEND. Each siRNA carrier and erythrocytes were mixed, and the absorbance of leaking hemoglobin was measured to evaluate the membrane-damaging action.
Figure 8:
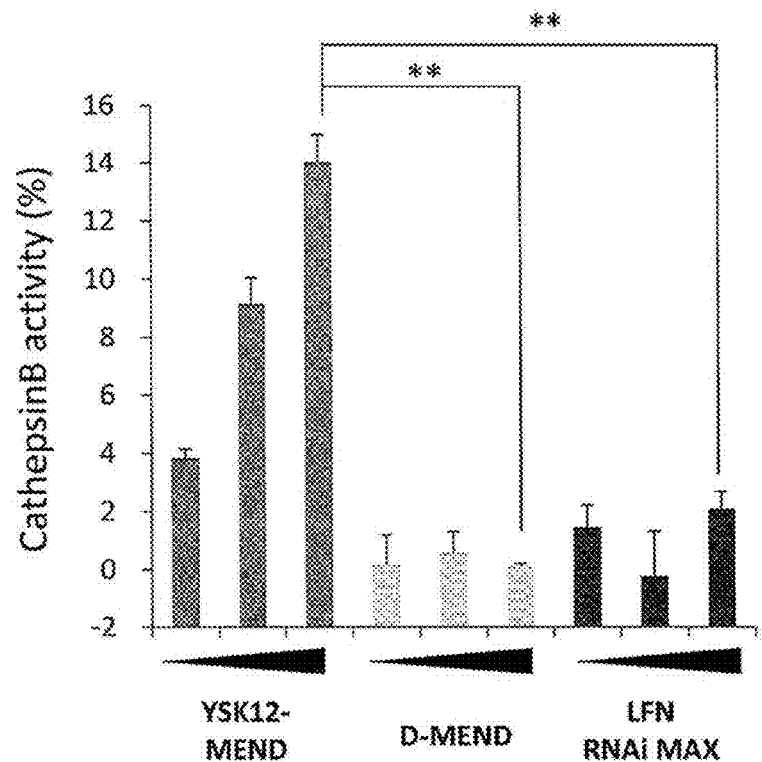
FIG. 8 A graph showing the results of evaluation of the membrane-damaging action of YSK12-MEND. By detecting the cathepsin B activity, direct endosome membrane-disrupting action was measured. The amount of siRNA was 10, 30, or 100 nM. The symbol ** indicates that there was significant difference $p<0.01$ (one-way ANOVA followed by Tukey-Kramer).

Intracellular kinetics of YSK12-MEND, D-MEND, and LFN RNAi MAX in the mouse dendritic cells were observed 6 hours later by using a confocal laser scanning microscope. As a result, many siRNAs labeled with red fluorescence were observed in the dendritic cells treated with YSK12-MEND, and therefore it was revealed that YSK12-MEND can extremely efficiently escape from endosomes (green fluorescence), and deliver siRNA to the cytoplasm (FIG. 6). Further, with YSK12-MEND, green fluorescence indicating acid compartments was not observed in the inside of the cells (FIG. 6), and high membrane disruption action was observed (FIGS. 7 and 8). Therefore, it was suggested that YSK12-MEND delivers siRNA to the cytoplasm by disrupting endosome membranes. On the basis of the above results, it is considered that YSK12-MEND shows high knockdown efficiency by significantly improved intracellular kinetics thereof, especially escape from endosomes, after being taken up by the cells through the high membrane disruption action.

Figure 9:
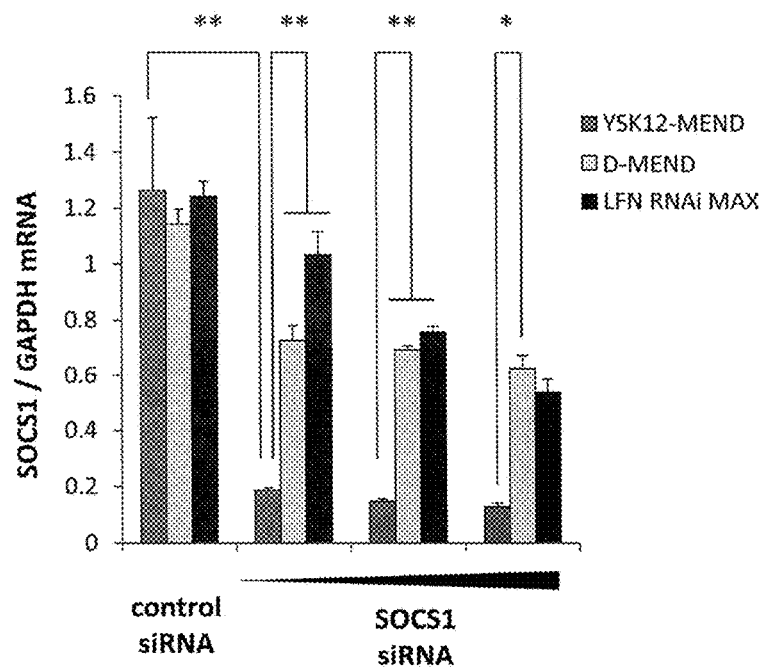
FIG. 9 A graph showing the results of SOCS1 knockdown with YSK12-MEND. The amount of siRNA was 3, 10, or 30 nM, and the amount of the control siRNA was 30 nM. The symbol * indicates that there was significant difference $p<0.05$, and ** indicates that there was significant difference $p<0.01$ (one-way ANOVA followed by Tukey-Kramer).
Figure 10:
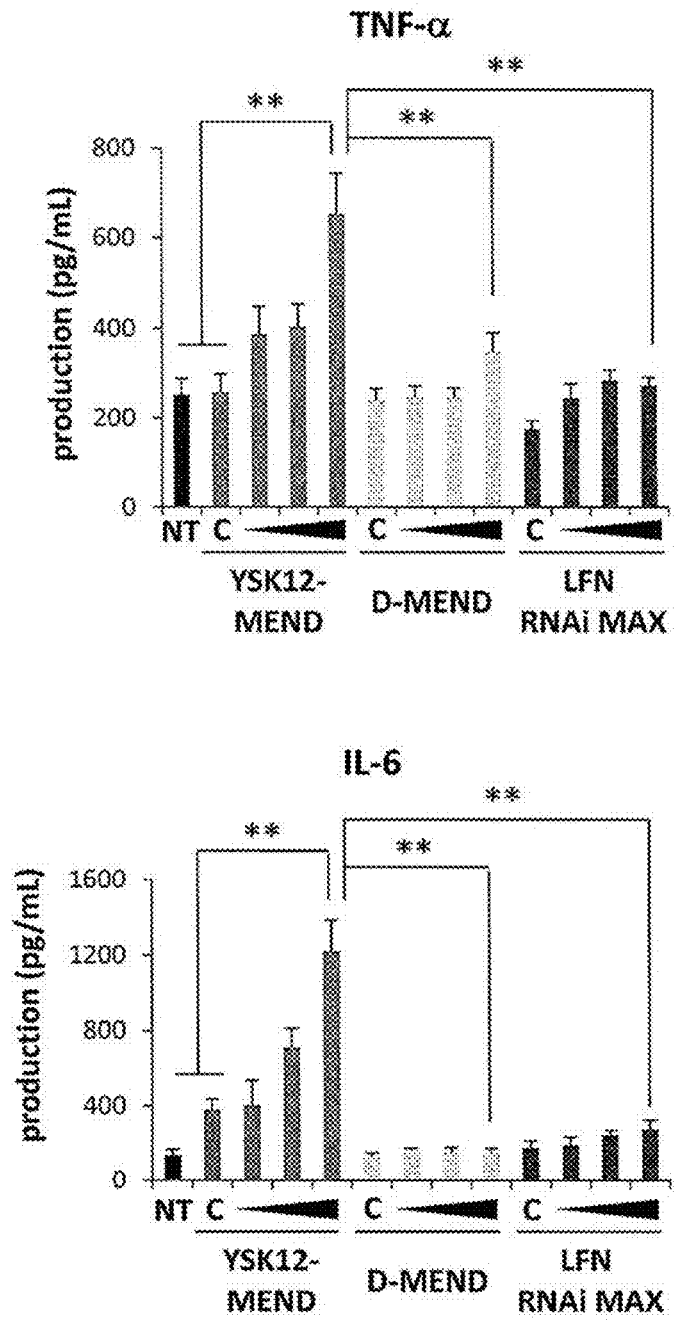
FIG. 10 Graphs showing the results of activation of immune function resulted from enhancement of the cytokine production ability of DC by knockdown of SOCS1 with YSK12-MEND. NT means no treatment, C means control siRNA (30 nM), and the amount of siRNA was 3, 10, or 30 nM. The symbol ** indicates that there was significant difference $p<0.01$ (one-way ANOVA followed by Tukey-Kramer).

Knockdown efficiencies of YSK12-MEND, D-MEND, and LFN RNAi MAX for SOCS1 in dendritic cells were evaluated. SOCS1 is a repressor of dendritic cells. As a result, YSK12-MEND showed a knockdown efficiency of about 80% at doses of 3, 10, and 30 nM (FIG. 9). Further, dendritic cells in which SOCS1 was knocked down were activated by adding IFN-γ, and amounts of cytokines (TNF-α and IL-6) produced in 24 hours were measured by the ELISA method. As a result, there were observed enhancements of TNF-α and IL-6 productions in a transfected siRNA amount-dependent manner (FIG. 10).

Figure 11:
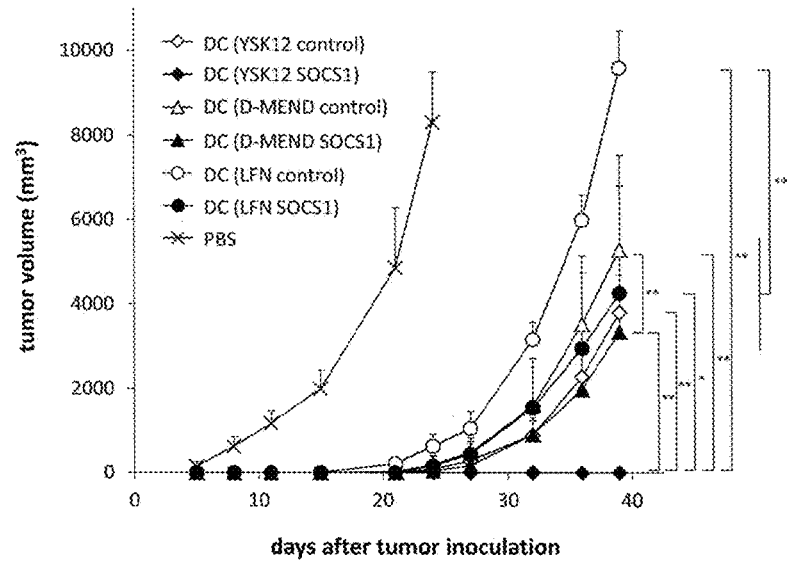
FIG. 11 A graph showing the results of evaluation of the prophylactic antitumor activity of YSK12-MEND. The symbol ** indicates that there was significant difference $p<0.01$ (one-way ANOVA followed by Tukey-Kramer).

Function of the regents as a cancer vaccine in dendritic cell therapy was evaluated. siRNA for SOCS1 or control siRNA was introduced into dendritic cells ($5\times10^5$) by using YSK12-MEND, D-MEND, and LFN RNAi MAX. The cells were allowed to take up ovalbumin (OVA) as an antigen, and used for immunization of mice by administration to the footpads, and one week thereafter, $1\times10^6$ of mouse lymphoma cells (E. G7-OVA) expressing OVA were hypodermically transplanted to the mice. Tumor volume was periodically measured. As a result, in the mouse groups administered with DCs in which SOCS1 was knocked down by using D-MEND or LFN RNAi MAX, significant antitumor activity was observed compared with the control group, but growth of the tumor could not be suppressed (FIG. 11). In contrast, in the mouse group administered with DCs in which SOCS1 was knocked down by using YSK12-MEND, engraftment of the tumor was completely suppressed (FIG. 11).

Example 3: Suppression of Gene Expression in THP-1 Cell (Human Monocyte Cell Line)

Figure 12:
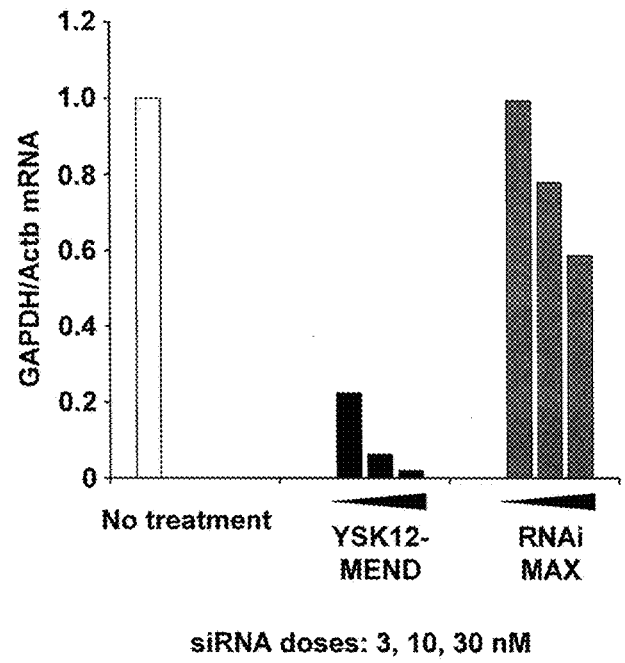
FIG. 12 A graph showing suppression of gene expression in the THP-1 cell (human monocyte cell line) with YSK12-MEND FIG. 13 A graph showing suppression of gene expression in the Jurkat cell (human T-cell cell line) with YSK12-MEND.

YSK12-MENDs enclosing GAPDH silencer siRNA or control silencer siRNA were prepared in the same manner as described in Example 2. The cells suspended in OPTI-MEND were inoculated into wells of a 12-well plate at a density of $6\times10^5$ cells/well, and YSK12-MEND or Lipofectamine RNAiMAX was added so that the final concentration of siRNA became 3, 10, or 30 nM. After culture for 2 hours, a culture medium containing serum was added, and the culture was continued for 22 hours. Then, the cells were collected, and mRNA amounts were evaluated by real-time RT-PCR. The results are shown in FIG. 12. It was demonstrated that YSK12-MEND can more efficiently attain gene knockdown compared with Lipofectamine RNAiMAX.

Example 4: Suppression of Gene Expression in Jurkat Cell (Human T-Cell Cell Line)

Figure 13:
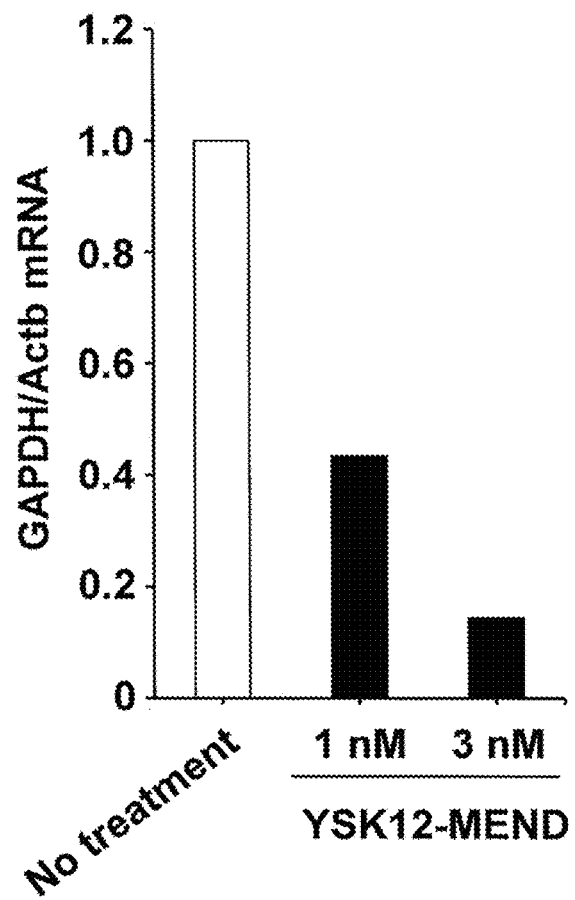

YSK12-MEND enclosing GAPDH silencer siRNA was prepared in the same manner as described in Example 2. The cells suspended in OPTI-MEND were inoculated into wells of a 12-well plate at a density of $6\times10^5$ cells/well, and YSK12-MEND was added so that the final concentration of siRNA became 1 or 3 nM. After culture for 2 hours, a culture medium containing serum was added, and the culture was continued for 22 hours. Then, the cells were collected, and mRNA amounts were evaluated by real-time RT-PCR. The results are shown in FIG. 13. It was demonstrated that YSK12-MEND can attain efficient gene knockdown at a level similar to that attained in THP-1 in Example 3.

INDUSTRIAL APPLICABILITY

The lipid membrane structure provided by the present invention can efficiently migrate intracellularly into an arbitrary cell for which introduction of siRNA is difficult, such as immunocytes including dendritic cell, and can efficiently escape from endosome. Therefore, it can efficiently release the encapsulated siRNA intracellularly to knock out a target gene with the siRNA. Accordingly, by using the lipid membrane structure of the present invention, an effective immunotherapy using siRNA, preferably a dendritic cell therapy, can be performed in cancer therapy. If a lipid membrane structure such as liposome is prepared by using the lipid compound provided by the present invention as a lipid component, extremely high endosomal escaping property thereof is attained, and efficient delivery of siRNA from the lipid membrane structure containing the lipid compound into the cytoplasm is achievable.

What is claimed is:
1. A lipid compound represented by the following formula (I), or a salt thereof:

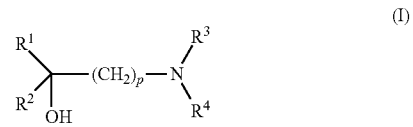

wherein, in the formula, $R^1$ and $R^2$ independently represent $CH_3$—$(CH_2)_n$—CH=CH—$CH_2$—CH=CH—$(CH_2)_m$— (n represents an integer of 3 to 5, and m represents an integer of 6 to 10), p represents an integer of 2 to 7, and $R^3$ and $R^4$ independently represent a $C_{1-4}$ alkyl group or a $C_{2-4}$ alkenyl group.

2. The lipid compound or a salt thereof according to claim 1, wherein n is 4, m is an integer of 7 to 9, p is an integer of 3 to 5, and $R^3$ and $R^4$ are independently $C_{1-4}$ alkyl groups.

3. The lipid compound or a salt thereof according to claim 1, wherein $R^1$ and $R^2$ are the same, n is 4, m is 8, p is 4, and $R^3$ and $R^4$ are methyl groups.

4. A method for delivering an siRNA intracellularly into a cell comprising intracellularly administering the siRNA together with a lipid membrane structure comprising the lipid compound or a salt thereof according to claim 1.

5. A lipid membrane structure for delivering an siRNA intracellularly into a cell, which encapsulates the siRNA inside thereof, and contains the lipid compound according to claim 1 as a lipid component.

6. The lipid membrane structure according to claim 5, which is a liposome.

7. The lipid membrane structure according to claim 5, which is used for knocking down a target gene in a dendritic cell.

8. The lipid membrane structure according to claim 7, which is used for knocking down a target gene in a dendritic cell in an immunotherapy comprising separating and collecting a dendritic cell from a patient, introducing an siRNA intracellularly into the dendritic cell in vitro, and administering the dendritic cell in which the target gene has been knocked down to the patient.

9. The lipid compound or a salt thereof according to claim 1, wherein $R^3$ and $R^4$ both represent $CH_3$.

10. The lipid compound or a salt thereof according to claim 1, wherein $R^3$ and $R^4$ both represent $CH_3$ and p represents an integer of 4.

11. The lipid compound or a salt thereof according to claim 1, wherein $R^3$ and $R^4$ both represent $CH_3$, p is 4, $R^1$ and $R^2$ are the same and m is 8.

12. The lipid compound or a salt thereof according to claim 1, wherein $R^3$ and $R^4$ independently represent a $C_{1-2}$ alkyl group or $C_2$ alkenyl group.

13. A lipid compound represented by the following formula (I), or a salt thereof:

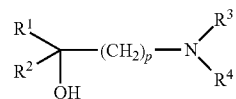

wherein, in the formula, $R^1$ and $R^2$, which are the same, represent $CH_3-(CH_2)_n-CH=CH-CH_2-CH=CH-(CH_2)_m-$, n represents an integer of 3 to 5, m is 8, p is 4, and $R^3$ and $R^4$ represent $CH_3$, and wherein the lipid compound is linked to a multifunctional envelope-type nano device (MEND).

14. A method for delivering an siRNA intracellularly into a cell comprising intracellularly administering the siRNA together with a lipid membrane structure comprising the lipid compound or a salt thereof according to claim 13.

15. A lipid membrane structure for delivering an siRNA intracellularly into a cell, which encapsulates the siRNA inside thereof, and contains the lipid compound according to claim 13 as a lipid component.

16. The lipid membrane structure according to claim 15, which is a liposome.

17. The lipid membrane structure according to claim 15, which is used for knocking down a target gene in a dendritic cell.

18. The lipid membrane structure according to claim 17, which is used for knocking down a target gene in a dendritic cell in an immunotherapy comprising separating and collecting a dendritic cell from a patient, introducing an siRNA intracellularly into the dendritic cell in vitro, and administering the dendritic cell in which the target gene has been knocked down to the patient.

19. The lipid compound or salt thereof according to claim 1, wherein $R^3$ and $R^4$ independently represent a $C_{1-2}$ alkyl group.

* * * * *